United States Patent [19]

Klemm

[11] Patent Number: Plant 7,122

[45] Date of Patent: Jan. 23, 1990

[54] GERANIUM PLANT NAMED MARLIMON

[76] Inventor: Siegfried Klemm, Hanfacker 8, D-7000 Stuttgart 50, Fed. Rep. of Germany

[21] Appl. No.: 246,284

[22] Filed: Sep. 12, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new and distinct geranium cultivar particularly distinguished by its very large, violet pink, half-filled clusters of about seventy-five large florets, each floret comprising from five to seven, broad, imbricated petals having a rounded apex and entire margins. This variety is a very bushy and compact plant with a relatively low height and medium growth rate and having a continuous and profusely blooming habit from early Spring through late midseason to Fall. The flower clusters stand on sturdy stalks about 13 cm. long and the foliage, of medium green leaves with faint zonation, stands about 17 cm. above the soil.

1 Drawing Sheet

BACKGROUND OF THE NEW PLANT

This new geranium cultivar originated as a seedling of the random pollinated geranium variety named 'Blues' (U.S. Plant Pat. No. 5,373) grown in my nursery at Stuttgart, West Germany, for the purpose of seed collection, this particular seedling having been selected for propagation from a group of seedlings of 'Blues' because of the very large size and violet pink coloration of its flower clusters. Asexual propagation of this selected plant was done by me and under my direction by means of cuttings at Stuttgart and carried on through several successive generations, which demonstrated conclusively that the distinctive characteristics of the selected plant would hold true from generation to generation and appeared to be firmly fixed. This new variety is being propagated for commercial purposes by means of cuttings at Stuttgart.

DESCRIPTION OF THE DRAWING

This new geranium cultivar is illustrated by the accompanying photographic drawing, which shows blooms, buds and foliage of the plant in full color, the colors shown being as nearly true to that herein specified as can be reasonably obtained by conventional, professional, photographic procedures.

DESCRIPTION OF THE NEW PLANT

The following is a detailed description of my new geranium cultivar as observed in my nursey at Stuttgart in the Spring of 1988, with color designations according to The R.H.S. Colour Chart of The Royal Horticultural Society of London, England.

THE PLANT

Origin: Seedling.

Parentage:

*Seed parent.*—The variety 'Blues' (unpatented).

*Pollen parent.*—Unknown.

Classification:

*Botanic.*—Pelargonium Zonale Hybrid.

*Commercial.*—Geranium.

Form: A compact and spreading bush.

Height: Relatively low.

Growth: Upright, bushy and compact with very good strength and a medium growth rate.

Branching character: Very good.

Flower stem length: About 13 cm.

Foliage:

*Quantity.*—Very abundant.

*Size of leaf.*—About 7 cm. wide and 6 cm. long.

*Leaf shape.*—Reniform with bicrenate margins.

*Texture.*—Smooth.

*Ribs and veins.*—Four main veins on each leaf.

*Color.*—Upper side — Medium green with weak zonation. Under side — Lighter green.

THE BUD

Size: Large.

*Diameter.*—About 12 mm.

*Length.*—About 12 to 15 mm.

Shape: Generally ovoid with pointed tip.

Rate of opening: Medium.

Color of petals: When sepals first divide, white pink. When petals begin to unfurl, pink violet.

Sepals:

*Number.*—Five.

*Shape.*—Lanceolate.

*Character.*—The sepals stand up when the flowers open.

*Color.*—Both inside and outside: Green.

Flower stem:

*Length.*—About 15 cm.

*Character.*—Erect and rigid.

*Color.*—Light green to medium green.

THE INFLORESCENCE

Blooming habit: Continuous and profusely from early Spring through midseason to Fall.

Flower cluster:

*Size.*—Very large with about seventy-five florets when filled.

*Stalk length.*—About 13 cm.

Florets:

*Size.*—Medium. Diameter — About 5 cm. Depth — About 1 cm. (It has no calyx.).

Borne: Singly on a stem of the umbel-formed cluster.

Shape: When the bloom first opens, cup-shaped. When the bloom matures, a flat cup.

Petalage:

*Number of petals.*—From five to seven.

*Form.*—Broad with rounded apex and entire margins.

*Arrangement.*—Imbricated.

*Texture.*—Soft.

*Aspect.*—Satiny.

*Color.*—Violet Pink, RHS 67-D.

Petaloids:

*Number.*—One or two.

*Size.*—About 4 mm.

*Color.*—Light violet pink.

Persistence: Very good; the petals stay on the stem about fifteen days.

Disease resistance: The plant has good resistance against Botrytis as observed in the area of Stuttgart, West Germany.

REPRODUCTIVE ORGANS

Stamens:

*Number.*—Seven.

*Arrangement.*—Around the ovaries.

*Anthers.*—Size: About 1.7 mm. Color: Orange.

*Filaments.*—Length: About 4 to 5 mm. Color: White.

*Pollen.*—Color: Orange.

Pistil:

*Number.*—One.

*Style.*—Length: About 5 mm. Color: White green.

*Stigma.*—Five cells. Color: Frosted Glas.

Character of ovaries: Normal for pelargonium.

THE FRUIT

Fertility: The fruit is very fertile.

Shape: Ovoid.

Color at maturity: Dark brown.

"Marlimon", with its violet pink blooming and bushy growing habit, is a new variety. The color is beautiful and there are very many flowers from Spring to Fall, the flowers and the flower clusters being very large and long lasting.

I claim:

1. The new and distinctive geranium cultivar, substantially has herein shown and described, and particularly characterized by its very many violet pink florets forming a close, compact group in a full, umbel-formed cluster.

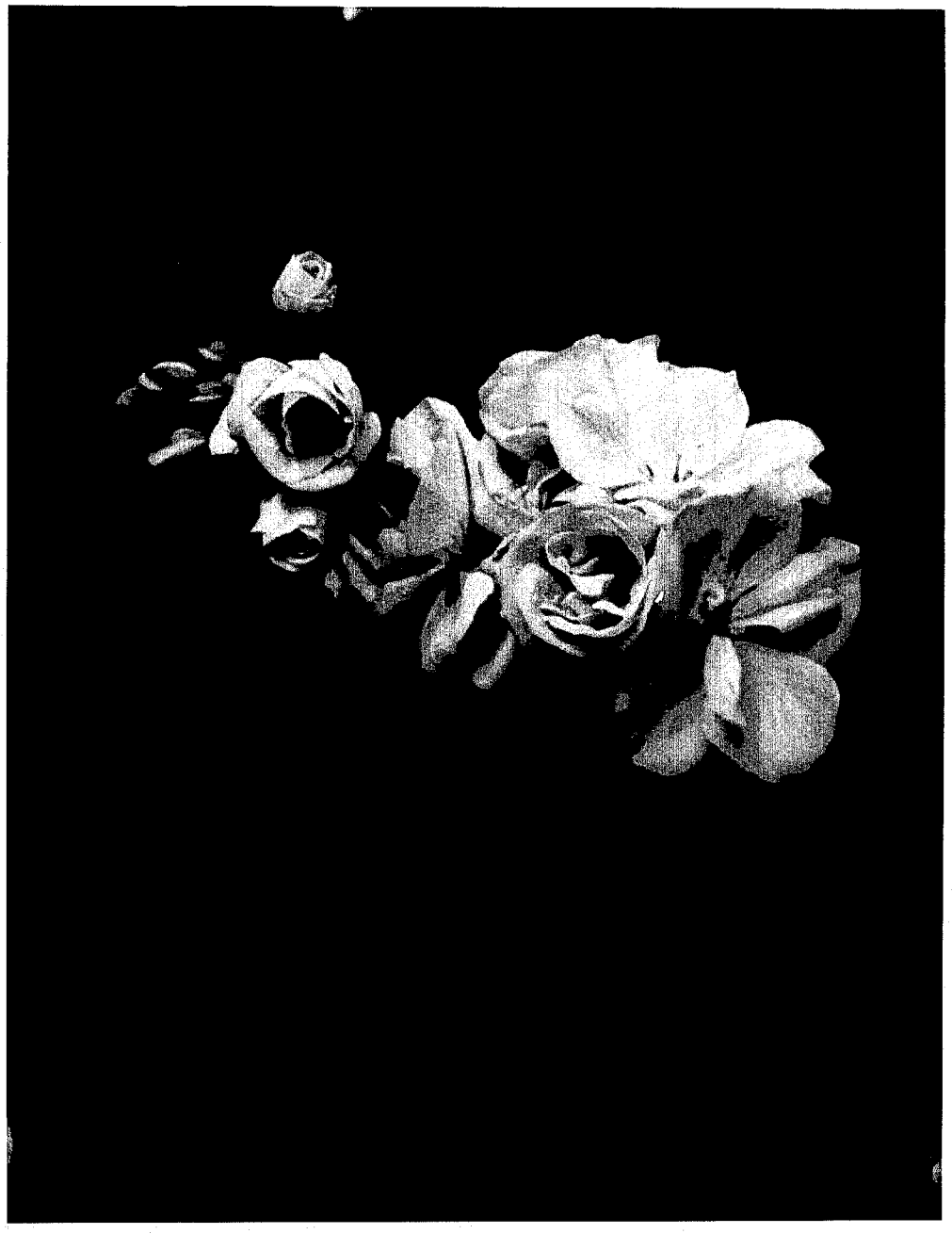

* * * * *